United States Patent [19]
Graether

[11] Patent Number: 5,634,884
[45] Date of Patent: Jun. 3, 1997

[54] APPARATUS FOR INSERTING A PUPIL EXPANDER

[75] Inventor: John M. Graether, Marshalltown, Iowa

[73] Assignee: Graether Development Corporation, Marshalltown, Iowa

[21] Appl. No.: 416,324

[22] Filed: Apr. 4, 1995

Related U.S. Application Data

[63] Continuation-in-part of Ser. No. 77,273, Jun. 17, 1993, Pat. No. 5,427,088, which is a continuation-in-part of Ser. No. 959,055, Oct. 9, 1992, Pat. No. 5,322,054, which is a continuation-in-part of Ser. No. 836,361, Feb. 18, 1992, Pat. No. 5,267,553.

[51] Int. Cl.⁶ ............................................. A61B 11/02
[52] U.S. Cl. ..................... 600/236; 600/210; 600/214; 600/215; 600/219; 606/107
[58] Field of Search ......................... 600/235–236, 600/210, 214–15, 217, 219; 606/107, 205, 206; 30/143, 162

[56] References Cited

U.S. PATENT DOCUMENTS

| | | | |
|---|---|---|---|
| 459,818 | 9/1891 | Pearson et al. | 606/205 X |
| 1,105,641 | 8/1914 | Feaster | 269/305 |
| 2,147,800 | 2/1939 | Sadowski | 269/305 |
| 2,464,114 | 3/1949 | Bloecher | 269/303 |
| 2,584,547 | 2/1952 | Cahn | 606/206 |
| 2,812,758 | 11/1957 | Blumenschein | 128/20 |
| 2,948,961 | 8/1960 | Ortner | 30/162 |
| 3,192,624 | 7/1965 | Gringer | 30/162 |
| 3,490,455 | 1/1970 | Illig . | |
| 3,807,393 | 4/1974 | McDonald | 128/20 |
| 4,037,589 | 7/1977 | McReynolds . | |
| 4,257,406 | 3/1981 | Schenk . | |
| 4,387,706 | 6/1983 | Glass | 128/20 |
| 4,452,235 | 6/1984 | Reynolds | 623/5 |
| 4,684,113 | 8/1987 | Douglas et al. | 269/303 |
| 4,693,245 | 9/1987 | Pao | 606/107 |
| 4,782,820 | 11/1988 | Woods | 128/20 |
| 4,906,247 | 3/1990 | Fritch | 606/107 |
| 4,911,158 | 3/1990 | Weatherly | 606/107 |
| 4,991,567 | 2/1991 | McCuen, II et al. . | |
| 5,066,297 | 11/1991 | Cumming | 606/107 |
| 5,099,578 | 3/1992 | Jan | 30/162 |
| 5,163,419 | 11/1992 | Goldman | 623/4 |
| 5,176,686 | 1/1993 | Poley | 606/107 |
| 5,188,125 | 2/1993 | Kilmer et al. | 606/166 |
| 5,217,464 | 6/1993 | McDonald | 606/107 |
| 5,222,972 | 6/1993 | Hill et al. | 606/205 |
| 5,267,553 | 12/1993 | Graether | 128/20 |
| 5,284,162 | 2/1994 | Wilk | 606/205 |
| 5,304,183 | 4/1994 | Gourlay et al. | 606/205 |
| 5,308,357 | 5/1994 | Lichtman | 606/206 |
| 5,395,378 | 3/1995 | McDonald | 623/6 |

*Primary Examiner*—Richard J. Apley
*Assistant Examiner*—Beverly M. Flanagan
*Attorney, Agent, or Firm*—Zarley, McKee, Thomte, Voorhees, & Sease

[57] ABSTRACT

A pupil expander insertion system for eye surgery includes a pupil expander insertion tool and an iris retracting glide. The insertion tool includes a housing having forward and rearward ends, a hollow chamber in which a piston is axially movable, and an aperture formed in the forward end that communicates with the hollow chamber. A retractable blade for holding a pupil expander in an elongated condition is journaled within the aperture and connected to the piston for longitudinal movement therewith. The forward end of the blade has a slot extending rearwardly, defining a pair of tines wherebetween the expander can be slidably inserted. A stationary hollow spatula surrounds the blade in the retracted position, contacting the pupil expander to slidingly urge it off the retracting blade. The glide has an elongated tongue with a folded tab on one end slidably inserted through a slot means in the other end.

16 Claims, 4 Drawing Sheets

APPARATUS FOR INSERTING A PUPIL EXPANDER

CROSS-REFERENCE TO A RELATED APPLICATIONS

This application is a continuation-in-part of application Ser. No. 08/077,273 filed Jun. 17, 1993, now U.S. Pat. No. 5,427,088, which is a continuation-in-part of application Ser. No. 07/959,055 filed Oct. 9, 1992, which is now U.S. Pat. No. 5,322,054 and which is a continuation-in-part of application Ser. No. 07/836,361 filed Feb. 18, 1992, which is now U.S. Pat. No. 5,267,553.

TECHNICAL FIELD

The present invention relates generally to instruments and methods utilized during eye surgery and more particularly to improved instruments and methods for retracting an iris and inserting a pupil expander within the interior chamber of the eye.

BACKGROUND OF THE INVENTION

The pupil expander of my issued U.S. Pat. No. 5,267,553 comprises a ring of silicone or other suitable soft plastic tubular material (e.g. Silastic®, Silicone, Dow Corning, Durometer Value of about 80) with an outside diameter of 8.2 mm and an inside diameter of 7.0 mm. The ring has a C-shaped cross-sectional configuration with the peripheral opening at the outside edge. The ring is formed into an incomplete circular shape, having a gap approximately 3.5 mm wide to permit surgical maneuvers with the ring. That gap is bridged by a strap between the open ends of the ring. There are also two ears therein with holes, which are used for manipulation of the device inside and outside of the eye.

In operation, when one desires to insert the pupil expander into the eye during a surgical procedure, the expander is first mounted on a carrier block or delivery case, as described in my issued U.S. Pat. No. 5,322,054 with said description being incorporated by reference herein. The pupil expander is then stretched into an elongated condition wherein the pupil expander is in a convenient position for removal and handling.

My previous U.S. Pat. No. 5,267,553 and 5,322,054 describe the use of forceps to manipulate the pupil expander. Because of the extremely small size of the pupil expander, the handling thereof is very delicate and sensitive, and ordinary forceps are not adapted for easy manipulation of the pupil expander. When forceps are used, a second tool, known as a spatula or lens manipulator, is required to hold the expander in place against the iris sphincter while the forceps tips are withdrawn so as to deposit the expander in the eye. Coordinated withdrawal of the forceps and spatula is a difficult and tedious task. There is a need for a single insertion tool that will both hold (or store) and slidably deposit the expander in the eye.

My co-pending application Ser. No. 07/959,055 describes a pupil expander inserting apparatus that combines the spatula and holding tool into one device. The apparatus for inserting a pupil expander disclosed therein provides selectively slidable movement of a blade with respect to a spatula fixed on a housing, but does not provide for smooth infinitely variable blade movement. Furthermore, because this apparatus is designed to be durable and reusable, it must be cleaned, sterilized, and loaded with another pupil expander before the next use. This apparatus is also composed almost entirely of specialized components which are generally expensive to produce.

It is therefore a principle object of this invention to provide a disposable apparatus for easily grasping and manipulating the pupil expander of my U.S. Pat. No. 5,267,553 so as to insert the expander into an eye without the need for a second instrument to manipulate the pupil expander.

A further object of this invention is to provide an improved storing and insertion tool for inserting a pupil expander into an eye.

A further object of this invention is to provide a self-retaining tool for holding the iris in a retraced position while a pupil expander is inserted into the eye.

A further object of this invention is to provide an insertion tool with a blade having a securing hole in which the strap of the pupil expander can be tucked so as to hold the expander without assistance from other structures on the insertion tool such that the assembly of the insertion tool, especially the loading of the pupil expander on the blade, can be broken down into subtasks and modules which facilitate more economical production and convenient surgical use.

These and other objects will be apparent to those skilled in the art.

SUMMARY OF THE INVENTION

The present invention involves a system for inserting a pupil expander in the eye. The system includes a pupil expander insertion tool and an iris retractor and methods of using the same.

The insertion tool includes an housing having forward and rearward ends, a hollow chamber in which a piston is axially movable, and an aperture formed in the forward end that communicates with the hollow chamber. Preferably, the housing and piston comprise a disposable syringe. A retractable blade for holding a pupil expander in an elongated condition is journaled within the aperture and connected to the piston for longitudinal movement therewith. The forward end of the blade has a slot extending rearwardly, defining a pair of substantially rigid parallel tines wherebetween the expander can be slidably inserted. A stationary hollow spatula surrounds the blade in the retracted position, contacting the pupil expander to slidingly urge it off the retracting blade.

Figures 10, 11, 12, 13, 14, 15, 16, 17:
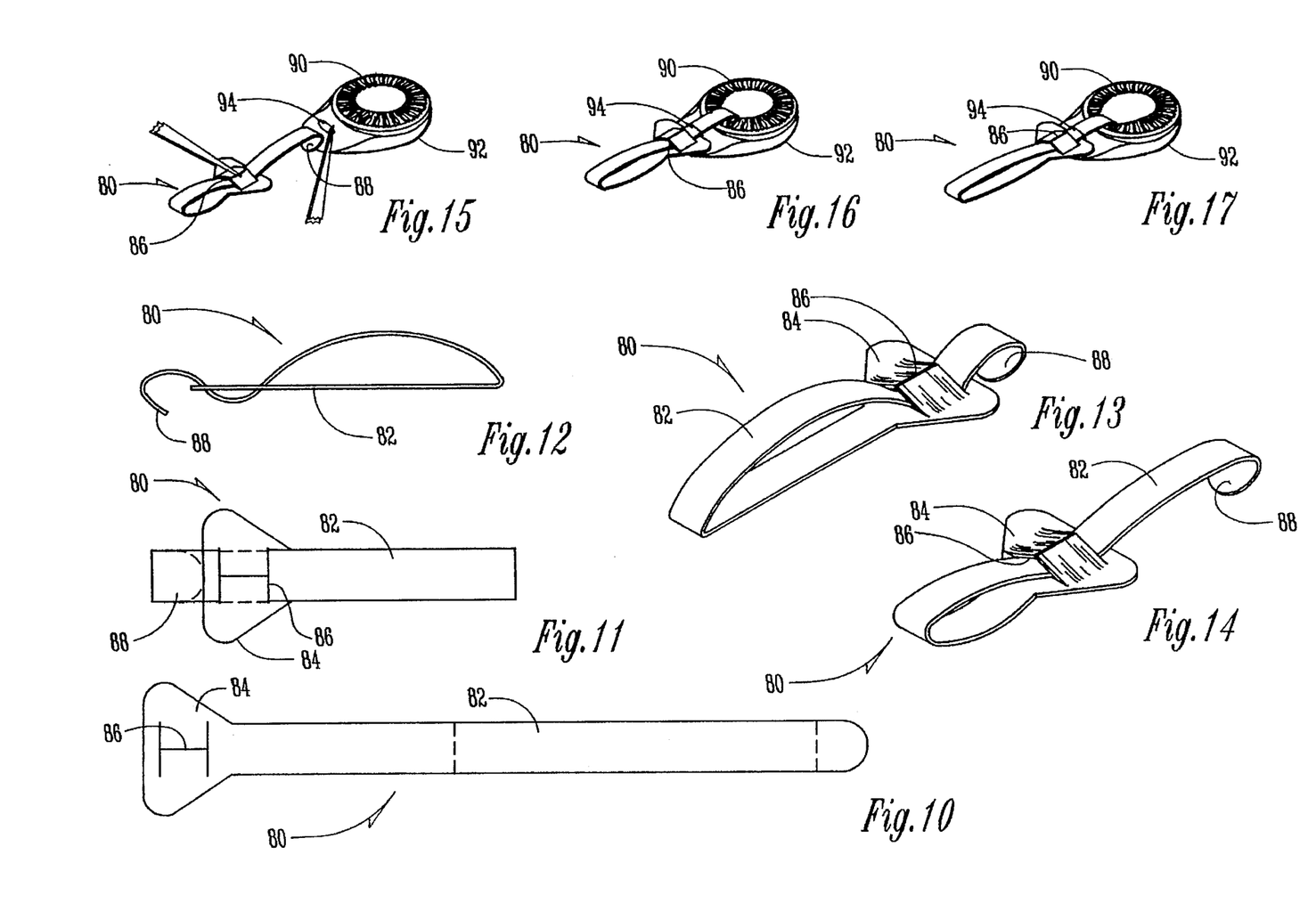
FIG. 10 is a large scale top plan view of the iris retractor of the present invention in its unfolded condition.
FIG. 11 is a top plan view of the iris retractor of FIG. 10 in its folded condition.
FIG. 12 is a side elevation view of the iris contractor as viewed from the right hand side of FIG. 11.
FIG. 13 is a perspective view of the iris retractor of FIG. 11 shown at a smaller scale.
FIG. 14 is a view similar to that of FIG. 13 but shows the tongue advanced through the slot.
FIG. 15 shows, at a smaller scale, the iris retractor about to be inserted through the wound.
FIG. 16 shows the tongue in engagement with the iris sphincter nearest the wound.
FIG. 17 shows the iris retractor in a position of exerting pressure on the sphincter as the tongue is moved from the position of FIG. 14 to the position of FIG. 13.

The iris retractor-glide is formed from sheet plastic approximately 0.07 mm thick that is transparent, tinted for visibility and relatively stiff in consistency. It must be biocompatable and approved for use in contact with human tissue. The device will be dye cut from the plastic sheeting and formed by a heat process to achieve the folds and contours shown (FIG. 12). It will be packaged with the pupil expander and loading tool, ready for use.

The modular construction of the insertion tool provides flexibility in the manufacture, assembly, and loading of the tool. The methods of assembly and loading are described in greater detail herein. The loaded needle module (cap, spatula, and blade with pupil expander loaded thereon) is preferably attached to a commercially available disposable syringe, thus reducing the cost of the tool.

The following method is employed for inserting a pupil expander. First, the iris retractor or glide is inserted through the incision already made by the surgeon. The retractor-glide is advanced through the incision until the folded end is in the space of the pupil. It is retracted, engaging the edge of the sphincter opposite the wound and retracting the iris sphincter toward the incision until the edge of the retracted pupil is adjacent to the internal aspect of the incision. The wedge shaped external portion of the retractor-glide fixes the device at the external wound and the natural elasticity of the plastic provides a force which retracts the iris as the retractor glide resumes its natural shape as the two surfaces again come into close proximity. The iris retractor is thereby self-retaining in the incision and frees the surgeon's hands for use elsewhere.

Next, the surgeon takes the pupil expander insertion tool of this invention in one hand and inserts the blade having a pupil expander loaded thereon through the incision and along the top surface of the iris retracting glide. The glide protects the retracted portion of the iris from being damaged by the insertion tool and eases the travel of the tool toward the counter pressure side of the iris. When the tool is in position adjacent the counter pressure side of the iris, the piston of the syringe is slowly withdrawn and the stationary spatula gently dislodges the pupil expander and deposits it on the iris sphincter muscle, which engages its C-shaped outer periphery. The insertion tool is withdrawn from the incision. When the retraction is no longer desired, the process of retracting the iris is reversed in order to release the glide.

DESCRIPTION OF THE PREFERRED EMBODIMENT

The present invention involves improvements to the basic slidable blade concept disclosed in my copending application Ser. No. 08/077,273, now U.S. Pat. No. 5,427,088. As will be understood from the following description, these improvements make it possible to conveniently produce and assembled components of the insertion tool in high volume. Furthermore, the present invention makes it possible to load the pupil expander on the blade separately, before the blade is assembled into the insertion tool. Thereafter, the complete device can be delivered in a sterile condition ready for use with the pupil expander fully loaded.

Figures 1, 2:
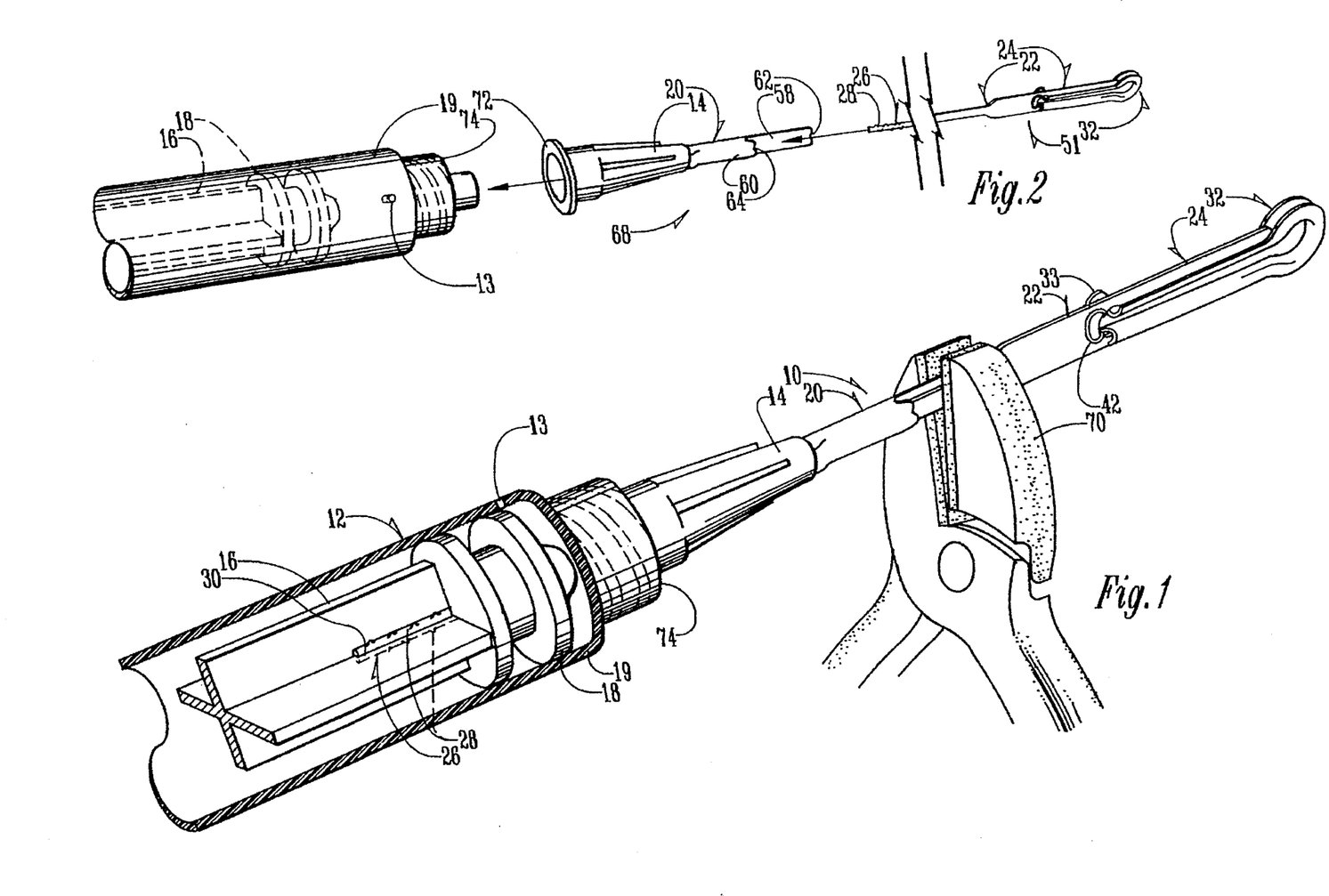
FIG. 1 is a perspective view of the fully assembled pupil expander insertion tool of this invention with a pupil expander mounted thereon.
FIG. 2 is an exploded view of the insertion tool of FIG. 1.

Referring now to the drawings, and more particularly to FIG. 1, the pupil expander insertion tool of the present invention is generally denoted by reference numeral 10. The tool 10 includes syringe 12 (having a vent hole 13), preferably a disposable sixteen gauge needle and disposable syringe that is well known in the art of medical instruments.

The disposable syringe 12 includes a piston 16 having a rubber stopper 18 on the forward end thereof. By applying force on piston 16, stopper 18 can be precisely moved axially within a hollow chamber inside tubular housing 19. The forward end of tubular housing 19 is adapted in a conventional manner to have a cap or cone 14 secured thereto. Cone 14 has a rearward end proximate to the stopper 18 and tapers inwardly to a forward end into which an elongated hollow spatula 20 is inserted and then fixed by conventional means.

Figures 3, 4:
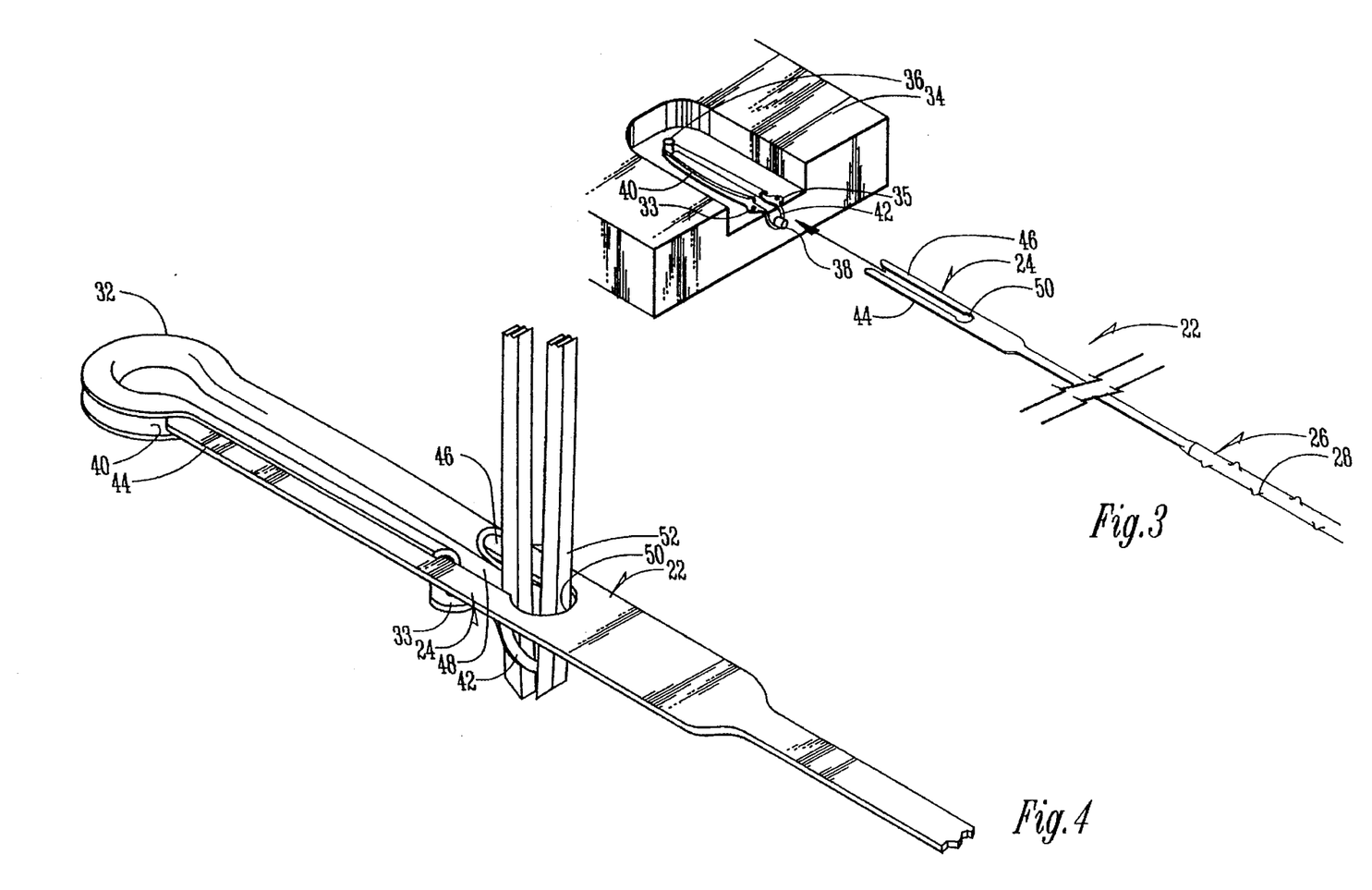
FIG. 3 is a top perspective view of a pupil expander on a carrier block about to be loaded on the blade of the insertion tool of this invention.
FIG. 4 is a top perspective view showing forceps being used to force the strap of the pupil expander through the securing hole in the detachable blade of this invention.

The insertion tool 10 further comprises an elongated blade 22 having a generally flat, forked, forward portion or end 24 and a cylindrical rear portion or end 26 (see FIGS. 2 and 3). The end 26 may also be referred to hereinafter as a shaft. The shaft 26 has a plurality of barbs 28 thereon. Preferably, barbs 28 extend in a generally radial direction from shaft 26. As seen in FIG. 1, the shaft 26 extends through the stopper 18 on the piston 16 of the syringe 12. Preferably, a predrilled hole 30 in the forward end of the piston 16 and through the stopper 18 accommodates the shaft 26. The barbs 28 engage the stopper 18 of the piston 16 so as to secure the blade 22 for concurrent axial movement therewith. Thus, when the piston 16 with stopper 18 attached thereto is pulled back or withdrawn to the left in FIG. 1, the blade 22 is also withdrawn or pulled to the left into spatula 20, which is stationary. Conversely, when the piston 16 is pushed to the right, the blade 22 moves to the right.

As best seen in FIG. 3, the blade 22 has forward and rearward portions or ends 24 and 26, respectively. The forward end 24 includes a longitudinal opening or slot 48 extending rearwardly which is preferably centrally located with respect to the longitudinal axis of the blade 22. The slot 48 defines a pair of forwardly projecting substantially rigid parallel tines 44 and 46 on the blade 22. The slot 48 extends far enough rearward that the elongated expander 32 can be slid into the slot to a point where only a very small portion of the elongated expander 32 extends beyond the tip of blade 22 (see FIG. 2 and 4).

As best seen in FIG. 3, a securing hole 50 is provided at the rearward end of slot 48. Hole 50 is positioned so as to be generally aligned with strap 42 when the pupil expander 32 is slid rearwardly as far as possible in the slot 48. Other than the securing hole 50, the details of the forked portion 24 are described in my co-pending application Ser. No. 08/077,273, now U.S. Pat. No. 5,427,088, and that description is incorporated herein by reference.

Referring now to FIG. 3, pupil expander 32 is shown in an elongated condition on a carrier block 34, as described in my issued U.S. Pat. No. 5,322,054, said description being incorporated herein by reference. The pupil expander 32 is stretched between a first post 36 and a retention post 38. When in the elongated condition shown, the pupil expander 32 can be conveniently removed and handled by the insertion tool 10 of the present invention.

The blade 22 can be inserted so that the forked portion 24 straddles the pupil expander 32 and extends alongside the peripheral opening 40. In the same manner as described in my co-pending application, the peripheral opening 40 of pupil expander 32 is engaged by tines 44 and 46 such that the pupil expander 32 is trapped in slot 48 of blade 22. The ears 33 and 35 of the pupil expander 32 extend laterally of transversely across each of the respective tines 44 and 46. The expander 32 can be removed from the carrier block 34 by moving blade 22 forward until the folded end of expander 32 can be raised off of the first post 36. Then blade 22 is moved rearwardly and downwardly to disengage a strap 42 of the expander 32 from the retention post 38.

In FIG. 4, a blunt tipped instrument, such as forceps 52, is used to bring or tuck the folded strap 42 through the hole 50. This is done so that the strap 42 is engaged in securing hole 50 and protrudes on the opposite side of the blade 22 than the ears 33 and 35. At any rate, ears 33 and 35 of the pupil expander 32 should rest against the top of the blade 22 and the strap 42 should protrude from or hang below the bottom of the blade 22. The blade 22 having pupil expander 32 loaded thereon in the manner just described constitutes a loaded blade module 51. Such a module can be easily assembled in a sterile and dust-free environment and placed in a sealed package for further assembly later. Preferably, the blade 22 has previously been polished in an ultrasound solution that will not cause rust to remove any debris from its fabrication. Similarly, the expander 32 can be pre-sterilized as is known in the art for silicone parts. If necessary, the entire module 51 (see FIG. 2) can also be cleaned and sterilized by known methods subsequent to assembly.

Figures 7, 9:
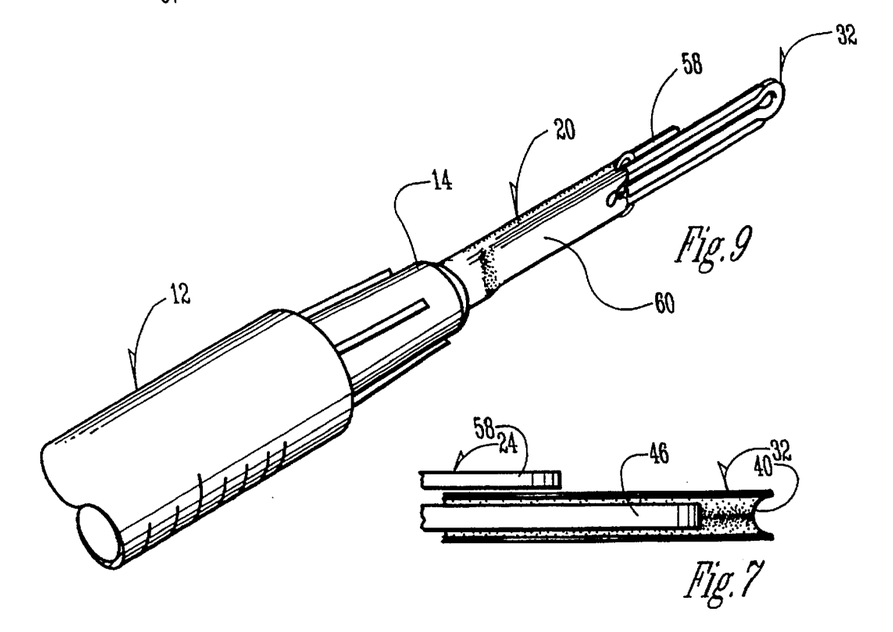
FIG. 7 is an enlarged view of the area denoted as 7—7 in FIG. 6 and shows the forward end of the insertion tool loaded with a pupil expander.
FIG. 9 is a perspective view of the bottom of the insertion tool of this invention with a pupil expander loaded thereon.
Figure 8:
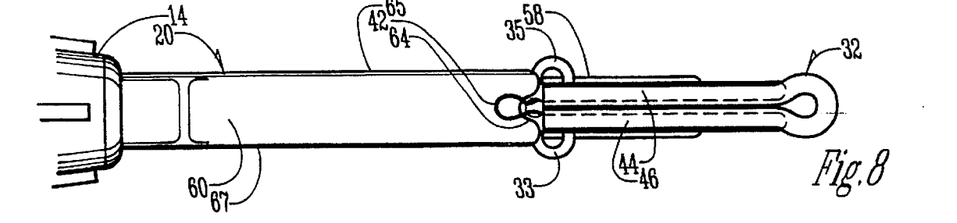
FIG. 8 is a bottom plan view of the forward portion of the insertion tool of this invention with a pupil expander mounted thereon.

When further assembly is desired, the blade 22 is rotated about its longitudinal axis so that the strap 42 protrudes upwardly therefrom (see FIG. 8). The hollow spatula 20 is inserted and fixed into the forward end of the cone 14. As best seen in FIGS. 2 and 5-9, the hollow spatula 20 has an elongated upper portion 58 and a truncated lower portion 60, each having a notch, 62 and 64 respectively, formed in the forward end thereof. Preferably, portions 58 and 60 are spaced apart by the side surfaces of the spatula and the forward end of the spatula 20 is flattened into an oblong cross-section approximately 2.0 mm by 1.15 mm. The optimal spacing between portions 58 and 60 for slidingly receiving the expander 32 between the spatula 20 and the blade 22 is provided. Preferably, a spacing structure interposed therebetween comprising a dent or depression 66 is formed in one or more of the portions 58 and/or 60 (see FIGS. 5 and 6). The depression 66 is disposed above and adjacent to the forward end of the lower truncated portion 60. Therefore, the pupil expander 32 and ears 33 and 35 thereon can easily slide between blade 22 and the upper portion 58 of the spatula 20. To help hold the pupil expander 32 on the insertion tool 10, the top portion 58 of the spatula 20 has an elongated, generally longitudinal top extension 61 that is wider than the (width across both tines 44 and 46, and thereby wider than the width of the slot 48 (see FIG. 5).

The rear portion of the spatula 20 preferably has a generally circular cross-section so as to be conveniently inserted in the forward end of cone 14, but other types of cross-sections can be utilized without detracting from the invention.

Figure 5:
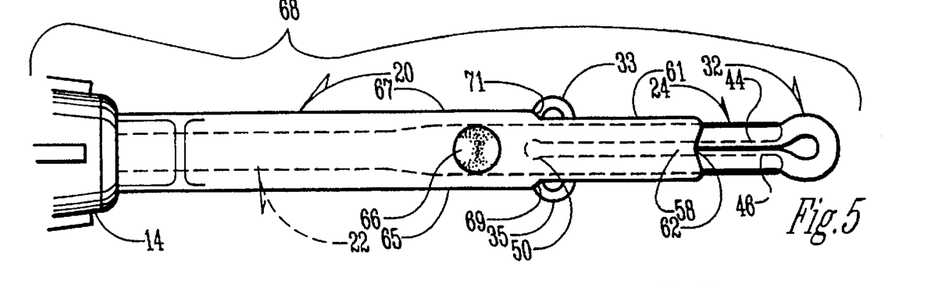
FIG. 5 is a top plan view of the forward portion of the insertion tool of this invention loaded with a pupil expander.
Figure 6:
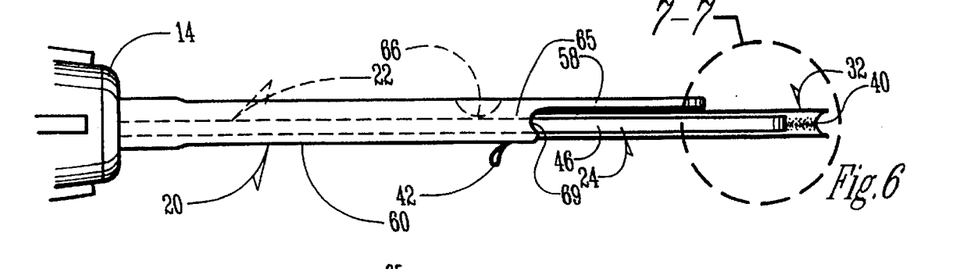
FIG. 6 is a side elevation view of the forward portion of the insertion tool of this invention loaded with a pupil expander.

In FIGS. 5 and 6, the side surfaces 65 and 67 of the spatula 20 have their leading edges equipped with arcuate, rearwardly extending notches 69 and 71, respectively. The notches are useful for clearance as shown in FIGS. 5, 8 and 9. Furthermore, the notches 69 and 71 allow the ears 33 and 35 of pupil expander 10 to extend laterally without interference or pinching. They also help prevent pinching of the expander 32 as the spatula 20 urges it longitudinally forward and off of the blade 22. Yet, as best understood from FIGS. 5-9, the blade 22 will be retracted into the spatula 20 when the piston 16 of syringe 12 is pulled rearwardly. This action causes the spatula 20 to contact the ears 33 and 35 and strap 42, which are gently moved forwardly until the pupil expander 32 comes out of slot 48 and thus off the tines 44 and 46 of blade 22. The clearance provided by depression 66 ensures that the expander 32 does not bind against the spatula 20 or the blade 22 as it comes off of the blade 22. The pulling of strap 42 through securing hole 50 also ensures that the portion of the pupil expander 32 disposed on the other side of the blade will ride closer to blade 22 than the spatula 20.

As seen in FIGS. 2 and 8, the shaft 26 of blade 22 is then inserted into the forward end of the hollow spatula 20 until the strap 42 of the pupil expander 32 rests in the notch 64 of the truncated lower portion 60. Preferably, the strap 42 is not folded back onto itself by the spatula 20. With the loaded blade module 51 in the position shown in FIG. 8, the strap 42 of the expander 32 protrudes upwardly from notch 64. On the other hand, ears 33 and 35 rest in the space between the elongated upper portion 58 of the spatula 20 and the blade 22. When so assembled, the shaft 26 protrudes from the rearward ends of the spatula 20 and the cone 14. A loaded needle module 68 has been formed, including the blade 22, the expander 32 thereon, the cone 14, and spatula 20.

The protruding shaft 26 is aligned with the pre-drilled hole 30 in the stopper 18 and piston 16. Then the loaded needle module 68 is pushed through an aperture or fastening bore 74 into the forward end of a standard sixteen gauge disposable needle and syringe 12 until the shaft 26 bottoms out in predrilled hole 30 and barbs 28 engage the stopper 18 of the syringe 12, as shown in FIG. 1. The syringe piston 16 is pushed forward into the shaft 26 of the blade 22 while the loaded needle module 68 is held against axial movement by padded pliers 70 or a similar suitable conventional holding device. Barbs 28 engage the stopper 18 and secure the blade 22 of the loaded needle module 68 for movement with the piston 16. Alternately, the shaft might be secured to the piston with an adhesive. The cone 14 and the spatula 20 affixed thereto are attached to the syringe 12 in a conventional manner by a flange 72 on the base of the cone 14. Preferably, the flange 72 tightly and/or threadably engages a fastening bore 74 on the syringe 12. Finally, the piston 16 may need to be repositioned slightly so that the tool 10 is ready for insertion into the eye as shown in FIG. 9. Preferably, the piston 16 should be pushed forward fully within the syringe so that the rubber stopper 18 rests against the bottom of the syringe 12.

The lower portion 60 of the spatula 20 has a notch 64 at the forward or truncated end thereof. Notch 64 accommodates the strap 42 of pupil expander 32 when the blade 22 is fully inserted into the spatula 20. The entire insertion tool with the expander in a loaded position will be delivered in a formed transparent case that will prevent displacement of the expander during shipping and handling or as it is removed from the container for use.

The process of inserting a tool loaded with the pupil expander into the patient's eye and depositing the expander is well described, in my co-pending application 08/077,273, now U.S. Pat. No. 5,427,088, and said description is incorporated herein by reference. The present invention provides a pupil expander insertion tool that can be easily pre-assembled, completely or in the modules described. The tool (or modules thereof) can be sterilized, and packaged for later use in the operating room. Of course, it may be desirable to set a shelf-life in the same conventional manner that is done with other sterilized goods.

FIG. 10 shows an iris retractor and glide 80, which serves as an accessory to the pupil expander insertion tool 10. The iris retractor-glide 80 can also be used in conjunction with other surgical instruments or tools, or whenever the surgeon desires to manipulate, retract, and/or hold the iris 90 of the patient's eye 92 in a particular position. The iris retractor-glide 80 (FIGS. 10-17), as previously indicated is formed from sheet plastic approximately 0.07 mm thick that is transparent, tinted for visibility and relatively stiff in consistency. It must be biocompatible and approved for use in contact with human tissue. The device will be dye cut from the plastic sheeting and formed by a heat process to achieve the folds and contours shown. It will be packaged with the pupil expander and loading tool, ready for use. The glide 80 has a tongue 82 that is 22 mm long and 1.25 mm wide except for the elongated triangular portion 84. The glide 10 is 0.10 mm thick. An I-shaped slot 86 in portion 84 is best shown in FIGS. 10 and 11. A folded tab 88 is formed in tongue 82 at the end opposite to portion 84.

FIGS. 15-17 illustrate the use of the iris retractor-glide 80 of this invention. As disclosed in my issued U.S. Pat. No. 5,267,553, a generally lateral incision 94 is made in the tissue adjacent the eye 92 at a twelve o'clock position with respect to the patient's body.

The retractor-glide will be picked up with a smooth (tying) forceps and the tongue of the retractor will be advanced through the slot as shown in FIG. 15. Grasping the device will fixate the tongue 82 relative to the triangular portion or stop and allow the tongue to be advanced through the wound. (FIG. 16). When the folded or redoubled tab 88 at the end of the tongue 82 advances into the pupil, the leading edge engages the iris sphincter closest to the wound. With the triangular portion 84 of the device resting against the outer aspect of the wound, the tongue 82 is withdrawn through the slot 86 allowing the natural elasticity of the plastic to cause the retractor-glide to flatten so that the device resumes the shape shown in FIGS. 13 or 17. That "resting" or unstressed state will sustain the forces on the iris sphincter that maintain its retraction toward the wound. As the insertion tool containing the pupil expander is advanced through the wound and is brought into a horizontal position on top of the retractor-glide, it will further fix the glide in place by pressure on the tongue 82 and on the redoubled or folded tab 88 beneath the iris, preventing displacement of the sphincter from the retractor-glide. The retractor-glide will then provide the counter traction necessary to allow the advancing pupil expander to stretch the miotic pupil until it reaches a size that will accommodate the pupil expander's circumference. It will also cause the pupil to elongate until it is in close proximity to the slot in the pupil expander, separated only the tines of the movable blade. As the blade is withdrawn within the cavity of the insertion tool, the slot in the pupil expander will move directly onto the adjacent sphincter edge, driven by the natural elasticity of the pupil expander as it is freed from the constraints of the slide. With guidance from the spatula tip of the tool, the pupil expander can be coaxed onto the sphincter until the fenestrated tabs or ears rest upon the surface of the iris adjacent to the terminal portion of the retractor-glide. At that point, the tool is removed entirely and the retractor-glide is again advanced toward the center of the pupil, freeing it from the iris. It may then be withdrawn from the eye or alternatively, it can be repositioned over the strap of the pupil expander to act as a guide for the phacoemulsifier.

Next, the surgeon takes the pupil expander insertion tool 10 of this invention in one hand and inserts the front of the loaded needle module 68 through the incision 94 and along the top surface of the iris retracting glide 80. The glide 80 protects the retracted portion of the iris 90 and allows the pupil to be stretched and elongated until the edge of the sphincter muscle (pupil) lies in close proximity to the slot in the pupil expander. When the tool 10 is in position adjacent the iris sphincter at the counter pressure side of the iris 90, the piston 16 of the syringe 12 is slowly withdrawn and the stationary spatula 20 gently dislodges the pupil expander 32 from blade 22 until the expander 32 is deposited on the iris sphincter muscle, which engages its C-shaped outer periphery 40. The insertion tool 10 is withdrawn from the incision 106. When retraction is no longer desired, the process of retracting the iris 90 is reversed in order to release the glide 80.

Whereas the invention has been shown and described in connection with the preferred embodiments thereof, it will be understood that modifications, substitutions, and additions may be made which are within the intended broad scope of the following claims. From the foregoing, it can be seen that the present invention accomplishes at least all of the stated objectives.

What is claimed is:

1. A pupil expander insertion tool, comprising: an elongated housing having forward and rearward longitudinal ends, and a hollow chamber within said housing;

a retractable blade for holding a pupil expander in an elongated condition, operably mounted in said hollow chamber for longitudinal slidable movement therewithin;

said housing having an aperture formed in the forward end thereof communicating with said hollow chamber;

said retractable blade including a forward portion and a rearward portion, the rearward portion slidably journaled within said aperture for selective slidable movement between an extended position projecting forwardly from the forward end, and a retracted position within said aperture;

an axially movable elongated piston slidably disposed in said hollow chamber and connected to said rearward portion of said blade for selectively sliding said blade between said retracted and extended positions;

said forward portion of said blade including a forward end having a slot formed therein extending rearwardly and defining a pair of forwardly projecting, substantially rigid tines which are substantially parallel to one another and wherebetween the pupil expander can be slidably inserted, said slot having a width;

said forward portion of said blade having a securing hole at a rearward end of said slot adapted to hold a strap of the pupil expander so that the pupil expander remains on said blade in the absence of outside forces, said securing hole having a diameter greater than said width of said slot; and an elongated hollow spatula having a forward end and a rearward end, said rearward end of said spatula being fixed to said forward end of said housing and laterally surrounding said retractable blade in said retracted position, such that when said blade is withdrawn to a retracted position by said piston the pupil expander held on said blade will be slidingly urged off said forward end of said blade by contact with said spatula.

2. The insertion tool of claim 1 wherein said housing and said piston form a disposable syringe.

3. The insertion tool of claim 1 wherein said spatula has top and bottom portions disposed around said blade and a depression in at least one of said top and bottom portions extends toward said blade and maintains sufficient space between said top surface of said spatula and said blade to slidably accommodate the pupil expander therebetween.

4. The insertion tool of claim 3 wherein said depression is in said top portion of said spatula and is dimensioned to provide approximately 0.25 mm clearance between said spatula and said blade.

5. The insertion tool of claim 1 wherein said rearward portion of said blade has a generally circular cross-section and a plurality of generally radially extending barbs thereon for engaging said piston and preventing forward axial movement of said blade relative to said piston.

6. The insertion tool of claim 1 wherein said forward end of said spatula has a centrally disposed notch therein.

7. The insertion tool of claim 1 wherein said spatula has opposite side surfaces, said side surfaces having forward and rearward ends, said forward ends of said side surfaces having leading edges with arcuate rearwardly extending notches therein for selectively contacting and urging forward said pupil expander.

8. The insertion tool of claim 1 wherein said forward end of said spatula has an elongated top extension having a width greater than the width across said tines of said blade and thereby greater than the width of the slot.

9. In combination, a pupil expander and a blade for holding said pupil expander in an elongated condition, said pupil expander including a ring having a gap therein bridged by a strap thereacross, said ring having a C-shaped cross-section forming an outwardly disposed peripheral opening, said blade comprising:

an elongated blade having a forward end and a rearward end;

said forward end of said blade having a longitudinal slot therein extending rearwardly so as to define two spaced apart substantially rigid and substantially parallel tines adjacent said slot;

said slot being of sufficient width to slidingly receive said pupil expander in an elongated condition between said tines with said tines fitting into said peripheral opening; and said blade having a securing hole therein for tucking said strap thereinto, said securing hole being located at a rearward end of said slot;

whereby said pupil expander in an elongated condition slid onto said blade is held in place on said blade until slidably and forcibly displaced therefrom.

10. The pupil expander holding apparatus of claim 9 wherein said rearward end of said elongated blade has a plurality of generally radially protruding barbs disposed thereon and a circular cross-section.

11. The pupil expander holding apparatus of claim 9 wherein said securing hole has a diameter greater than the width of said slot.

12. A pupil expander insertion tool, comprising:

an elongated housing having forward and rearward longitudinal ends, and a hollow chamber within said housing;

a retractable blade for holding a pupil expander in an elongated condition, operably mounted in said hollow chamber for longitudinal slidable movement therewithin;

said housing having an aperture formed in the forward end thereof communicating with said hollow chamber;

said retractable blade including a forward portion and a rearward portion, the rearward portion slidably journaled within said aperture for selective slidable movement between an extended position projecting forwardly from the forward end, and a retracted position within said aperture;

an axially movable elongated piston slidably disposed in said hollow chamber and connected to said rearward portion of said blade for selectively sliding said blade between said retracted and extended positions;

said forward portion of said blade including a forward end having a slot formed therein extending rearwardly and defining a pair of forwardly projecting, substantially rigid parallel tines which are wherebetween the pupil expander can be slidably inserted;

said forward portion of said blade having a securing hole at a rearward end of said slot adapted to hold a strap of the pupil expander so that the pupil expander remains on said blade in the absence of outside forces; and an elongated hollow spatula having a forward end and a rearward end fixed to said forward end of said housing and laterally surrounding said retractable blade in said retracted position, such that when said blade is withdrawn to a retracted position by said piston the pupil expander held on said blade will be slidingly urged off said forward end of said blade by contact with said spatula;

said rearward portion of said blade having a generally circular cross-section and a plurality of generally radially extending barbs thereon for engaging said piston and preventing forward movement of said blade relative to said piston.

13. A pupil expander insertion tool, comprising:

an elongated housing having forward and rearward longitudinal ends, and a hollow chamber within said housing;

a retractable blade for holding a pupil expander in an elongated condition, operably mounted in said hollow chamber for longitudinal slidable movement therewithin;

said housing having an aperture formed in the forward end thereof communicating with said hollow chamber;

said retractable blade including a forward portion and a rearward portion, the rearward portion slidably journaled within said aperture for selective slidable movement between an extended position projecting forwardly from the forward end, and a retracted position within said aperture;

an axially movable elongated piston slidably disposed in said hollow chamber and connected to said rearward portion of said blade for selectively sliding said blade between said retracted and extended positions;

said forward portion of said blade including a forward end having a slot formed therein extending rearwardly and defining a pair of forwardly projecting, substantially rigid parallel tines which are wherebetween the pupil expander can be slidably inserted;

said forward portion of said blade having a securing hole at a rearward end of said slot adapted to hold a strap of the pupil expander so that the pupil expander remains on said blade in the absence of outside forces; and an elongated hollow spatula having a forward end and a rearward end fixed to said forward end of said housing and laterally surrounding said retractable blade in said retracted position, such that when said blade is withdrawn to a retracted position by said piston the pupil expander held on said blade will be slidingly urged off said forward end of said blade by contact with said spatula;

said spatula having opposite side surfaces, said side surfaces having forward and rearward ends, said forward end of said side surfaces having leading edges with arcuate rearwardly extending notches therein for selectively contacting and urging forward said pupil expander.

14. A pupil expander insertion tool, comprising:

an elongated housing having forward and rearward longitudinal ends, and a hollow chamber within said housing;

a retractable blade for holding a pupil expander in an elongated condition, operably mounted in said hollow chamber for longitudinal slidable movement therewithin;

said housing having an aperture formed in the forward end thereof communicating with said hollow chamber;

said retractable blade including a forward portion and a rearward portion, the rearward portion slidably journaled within said aperture for selective slidable movement between an extended position projecting forwardly from the forward end, and a retracted position within said aperture;

an axially movable elongated piston slidably disposed in said hollow chamber and connected to said rearward portion of said blade for selectively sliding said blade between said retracted and extended positions;

said forward portion of said blade including a forward end having a slot formed therein extending rearwardly and defining a pair of forwardly projecting, substantially rigid parallel tines which are wherebetween the pupil expander can be slidably inserted;

said forward end of said blade having a securing hole at a rearward end of said slot adapted to hold a strap of the pupil expander so that the pupil expander remains on said blade in the absence of outside forces; and an elongated hollow spatula having a forward end and a rearward end fixed to said forward end of said housing and laterally surrounding said retractable blade in said retracted position, such that when said blade is withdrawn to a retracted position by said piston the pupil expander held on said blade will be slidingly urged off said forward end of said blade by contact with said spatula;

said forward end of said spatula having an elongated top extension having a width greater than the width across said tines of said blade and thereby greater than the width of the slot.

15. In combination, a pupil expander and a blade for holding said pupil expander in an elongated condition, said pupil expander including a ring having a gap therein bridged by a strap thereacross, said ring having a C-shaped cross-section forming an outwardly disposed peripheral opening, said blade comprising:

an elongated blade having a forward end and a rearward end;

said forward end of said blade having a longitudinal slot therein extending rearwardly so as to define two spaced apart substantially rigid parallel tines adjacent said slot;

said slot being of sufficient width to slidingly receive said pupil expander in an elongated condition between said tines with said tines fitting into said peripheral opening; and said blade having a securing hole therein for tucking said strap thereinto, said securing hole being located at a rearward end of said slot;

whereby said pupil expander in an elongated condition is held in place on said blade until slidably and forcibly displaced therefrom;

said rearward end of said elongated blade having a plurality of generally radially protruding barbs disposed thereon and a circular cross-section.

16. In combination, a pupil expander and a blade for holding said pupil expander in an elongated condition, said pupil expander including a ring having a gap therein bridged by a strap thereacross, said ring having a C-shaped cross-section forming an outwardly disposed peripheral opening, said blade comprising:

an elongated blade having a forward end and a rearward end;

said forward end of said blade having a longitudinal slot therein extending rearwardly so as to define two spaced apart substantially rigid parallel tines adjacent said slot;

said slot being of sufficient width to slidingly receive said pupil expander in an elongated condition between said tines with said tines fitting into said peripheral opening; and said blade having a securing hole therein for tucking said strap thereinto, said securing hole being located at a rearward end of said slot;

whereby said pupil expander in an elongated condition is held in place on said blade until slidably and forcibly displaced therefrom;

said securing hole having a diameter greater than the width of said slot.

* * * * *